US 9,494,409 B2

(12) United States Patent
Schönleber et al.

(10) Patent No.: US 9,494,409 B2
(45) Date of Patent: Nov. 15, 2016

(54) TEST DEVICE FOR TESTING A BONDING LAYER BETWEEN WAFER-SHAPED SAMPLES AND TEST PROCESS FOR TESTING THE BONDING LAYER

(75) Inventors: Martin Schönleber, Aschaffenburg (DE); Berthold Michelt, Wiesbaden (DE)

(73) Assignee: Precitec Optronik GmbH (DE)

( * ) Notice: Subject to any disclaimer, the term of this patent is extended or adjusted under 35 U.S.C. 154(b) by 9 days.

(21) Appl. No.: 13/525,184

(22) Filed: Jun. 15, 2012

(65) Prior Publication Data

US 2012/0320380 A1    Dec. 20, 2012

(30) Foreign Application Priority Data

Jun. 17, 2011    (DE) .................. 10 2011 051 146

(51) Int. Cl.
| | |
|---|---|
| G01B 9/02 | (2006.01) |
| G01B 11/06 | (2006.01) |
| G01B 11/24 | (2006.01) |
| G01N 21/47 | (2006.01) |

(Continued)

(52) U.S. Cl.
CPC .......... G01B 9/02044 (2013.01); G01B 9/0203 (2013.01); G01B 9/02091 (2013.01); G01B 11/0625 (2013.01); G01B 11/2441 (2013.01); G01N 21/4795 (2013.01); G01N 21/8422 (2013.01); G01N 21/9501 (2013.01); *G01N 2021/8438* (2013.01)

(58) Field of Classification Search
CPC ................................ G01N 21/55; H04N 7/18
USPC .................... 356/451, 479; 600/425
See application file for complete search history.

(56) References Cited

U.S. PATENT DOCUMENTS

| | | |
|---|---|---|
| 4,861,131 A | 8/1989 | Bois et al. |
| 5,276,631 A | 1/1994 | Popovic et al. |
| 5,392,124 A | 2/1995 | Barbee |

(Continued)

FOREIGN PATENT DOCUMENTS

| | | |
|---|---|---|
| CN | 101393015 | 3/2009 |
| DE | 69622943 | 3/2003 |

(Continued)

OTHER PUBLICATIONS

Niklaus, et al. "Adhesive Wafer Bonding", Journal of Applied Physics, Applied Physics Reviews—Focused Review, 2006, vol. 99, No. 1, pp. 031101.1-031101.28.

(Continued)

*Primary Examiner* — Tarifur Chowdhury
*Assistant Examiner* — Jamil Ahmed
(74) *Attorney, Agent, or Firm* — Taylor English Duma LLP

(57) ABSTRACT

The invention relates to a test device for testing a bonding layer between wafer-shaped samples and a test process for testing the bonding layer. The test device comprises a measuring head for an OCT process that is configured to direct an optical measuring beam at a composite comprising at least two wafer-shaped samples with a bonding layer positioned between them. An optical beam splitter is configured to divert an optical reference beam as a reference arm for distance measurements. An evaluation unit is configured to evaluate layer thickness measurements without a reference arm and distance measurements with a reference arm. An optical switch device is configured to connect and disconnect the reference arm.

4 Claims, 6 Drawing Sheets

(51) Int. Cl.
    *G01N 21/84*    (2006.01)
    *G01N 21/95*    (2006.01)

(56) References Cited

U.S. PATENT DOCUMENTS

| | | | |
|---|---|---|---|
| 5,532,815 | A | 7/1996 | Kipman et al. |
| 5,691,540 | A | 11/1997 | Halle et al. |
| 5,905,572 | A | 5/1999 | Li |
| 6,099,522 | A | 8/2000 | Knopp et al. |
| 6,396,069 | B1 | 5/2002 | MacPherson et al. |
| 6,672,943 | B2 | 1/2004 | Vogtmann et al. |
| 6,673,654 | B2 | 1/2004 | Ohno et al. |
| 6,686,270 | B1 | 2/2004 | Subramanian et al. |
| 6,768,552 | B2 | 7/2004 | Takahashi et al. |
| 6,806,969 | B2 | 10/2004 | Clifford, Jr. et al. |
| 6,887,126 | B2 | 5/2005 | Brouillette et al. |
| 6,897,964 | B2 | 5/2005 | Takahashi et al. |
| 7,271,916 | B2 | 9/2007 | Jasapara et al. |
| 7,306,696 | B2 | 12/2007 | Lian et al. |
| 7,307,735 | B2 | 12/2007 | Hecht et al. |
| 7,477,401 | B2 | 1/2009 | Marx et al. |
| 7,525,732 | B2 | 4/2009 | Uehara et al. |
| 7,652,774 | B2 | 1/2010 | Lian et al. |
| 7,705,995 | B1 | 4/2010 | Johs et al. |
| 7,738,113 | B1 | 6/2010 | Marx et al. |
| 8,716,039 | B2 | 5/2014 | Dusemund |
| 8,982,339 | B2 | 3/2015 | Schonleber et al. |
| 9,295,391 | B1 | 3/2016 | Tearney |
| 9,297,645 | B2 | 3/2016 | Schonleber |
| 2002/0153500 | A1 | 10/2002 | Fordahl et al. |
| 2003/0016353 | A1 | 1/2003 | Detalle et al. |
| 2003/0090671 | A1 | 5/2003 | Takahashi et al. |
| 2004/0021874 | A1 | 2/2004 | Shimmick |
| 2004/0185582 | A1 | 9/2004 | Kueny |
| 2004/0262529 | A1* | 12/2004 | Yoshida et al. ............... 250/372 |
| 2005/0003642 | A1 | 1/2005 | Hecht et al. |
| 2005/0073692 | A1 | 4/2005 | De Groot |
| 2005/0140981 | A1* | 6/2005 | Waelti ........................... 356/479 |
| 2005/0237537 | A1 | 10/2005 | Leizerson et al. |
| 2005/0248771 | A1 | 11/2005 | Eussen et al. |
| 2006/0132790 | A1 | 6/2006 | Gutin |
| 2006/0194419 | A1 | 8/2006 | Araki |
| 2007/0046948 | A1 | 3/2007 | Podoleanu et al. |
| 2007/0086018 | A1 | 4/2007 | Shih et al. |
| 2007/0148792 | A1 | 6/2007 | Marx et al. |
| 2007/0188765 | A1 | 8/2007 | Zhao et al. |
| 2007/0231717 | A1 | 10/2007 | Rivers et al. |
| 2007/0258095 | A1 | 11/2007 | Oliver et al. |
| 2008/0013078 | A1 | 1/2008 | Podoleanu et al. |
| 2008/0151237 | A1 | 6/2008 | Lian et al. |
| 2009/0031792 | A1 | 2/2009 | Fan et al. |
| 2009/0059239 | A1 | 3/2009 | Hoffmann et al. |
| 2009/0250635 | A1 | 10/2009 | Sykora et al. |
| 2009/0257065 | A1 | 10/2009 | Hauger et al. |
| 2009/0273782 | A1 | 11/2009 | Yoo et al. |
| 2010/0007894 | A1 | 1/2010 | Suehira |
| 2010/0051068 | A1 | 3/2010 | Miyanari |
| 2010/0110376 | A1 | 5/2010 | Everett et al. |
| 2010/0157308 | A1 | 6/2010 | Xie |
| 2010/0265493 | A1 | 10/2010 | Jiang et al. |
| 2010/0283842 | A1* | 11/2010 | Guissin et al. ................. 348/68 |
| 2010/0321671 | A1 | 12/2010 | Marx et al. |
| 2011/0085136 | A1 | 4/2011 | Ferguson et al. |
| 2011/0180521 | A1 | 7/2011 | Quitter et al. |
| 2011/0222070 | A1 | 9/2011 | Nagai et al. |
| 2011/0292375 | A1 | 12/2011 | Marx et al. |
| 2012/0050723 | A1 | 3/2012 | Emtman et al. |
| 2012/0238869 | A1* | 9/2012 | Schmitt et al. ............... 600/425 |
| 2012/0257207 | A1* | 10/2012 | Marx et al. .................... 356/451 |
| 2013/0034918 | A1 | 2/2013 | Dusemund et al. |

FOREIGN PATENT DOCUMENTS

| | | |
|---|---|---|
| DE | 10319843 | 4/2004 |
| DE | 102004011189 | 9/2005 |
| DE | 102004052205 | 5/2006 |
| DE | 102005036719 | 2/2007 |
| DE | 102005052743 | 5/2007 |
| DE | 102008041062 | 4/2009 |
| DE | 102010000079 | 1/2010 |
| DE | 102008049821 | 4/2010 |
| DE | 102010016862 | 5/2010 |
| DE | 102010015944 | 7/2011 |
| DE | 102011081596 | 4/2012 |
| DE | 19525770 | 10/2012 |
| DE | 102011051146 | 10/2012 |
| DE | 102011055735 | 5/2013 |
| DE | 102012111008 | 5/2014 |
| EP | 0905476 | 3/1999 |
| EP | 1018632 | 7/2000 |
| EP | 1977850 | 10/2008 |
| EP | 2159535 | 3/2010 |
| FR | 2950441 | 3/2011 |
| GB | 1105819 | 3/1968 |
| JP | 6065963 | 4/1988 |
| KR | 1020080112436 | 12/2008 |
| TW | 200712585 | 4/2007 |
| TW | 200937005 | 9/2009 |
| WO | 9727613 | 7/1997 |
| WO | 2006028926 | 3/2006 |
| WO | 2007060441 | 5/2007 |
| WO | 2008010996 | 1/2008 |
| WO | 2011086490 | 7/2011 |
| WO | 2011141867 | 11/2011 |
| WO | 2014076649 | 5/2014 |

OTHER PUBLICATIONS

Rowland, et al. "Impact of polymer film thickness and cavity size on polymer flow during embossing: toward process design rules for nanoimprint lithography", Journal of Micromechanics and Microengineering, 2005, vol. 15, pp. 2414-2425.
Extended European Search Report for serial No. EP12172165, mailed Oct. 24, 2012, 5 pgs.
Schonleber German Examination Report for serial No. DE102011051146, filed Oct. 4, 2012, mailed Jan. 9, 2012, 6 pgs.
Taiwan Office Action for serial No. 101121622, filed Jun. 15, 2012, mailed May 21, 2014, 15 pgs.
Precitec Optronik Gmbh; Korean Notice of Preliminary Rejection for serial No. 10-2012-0064923, filed Jun. 18, 2012, mailed Oct. 30, 2014, 11 pgs.
Schoenleber; German Examination Report for serial No. DE102012102826, mailed Sep. 28, 2012, 14 pgs.
Schonleber, Martin; Final Office Action for U.S. Appl. No. 13/440,434, filed Apr. 5, 2012, mailed Feb. 10, 2014, 20 pgs.
Schonleber, Martin; Non Final Office Action for U.S. Appl. No. 13/440,434, filed Apr. 5, 2012, mailed Oct. 14, 2014, 16 pgs.
Schonleber, Martin; Non-Final Office Action for U.S. Appl. No. 13/440,434, filed Apr. 5, 2012, mailed Sep. 24, 2013, 34 pgs.
Schonleber, Martin; Notice of Allowance for U.S. Appl. No. 13/440,434, filed Apr. 5, 2012, mailed Feb. 12, 2015, 9 pgs.
Schonleber; U.S. Patent Application entitled: Apparatus and Method for Determining a Depth of a Region Having a High Aspect Ratio that Protrudes into a Surface of a Semiconductor Wafer having U.S. Appl. No. 13/440,434, filed Apr. 5, 2012, 21 pgs.
Schonleber; United Kingdom Search Report for serial No. GB1105819.5, filed Apr. 6, 2011, mailed Jul. 23, 2012, 4 pgs.
Dusemund, Claus; Issue Notification for U.S. Appl. No. 13/521,736, filed Jul. 11, 2012, mailed Apr. 16, 2014, 1 pg.
Dusemund, Claus; Non-Final Office Action for U.S. Appl. No. 13/521,736, filed Jul. 11, 2012, mailed Jul. 23, 2013, 18 pgs.
Dusemund, Claus; Notice of Allowance for U.S. Appl. No. 13/521,736, filed Jul. 11, 2012, mailed Dec. 27, 2013, 8 pgs.
Dusemund; International Preliminary Report on Patentability for serial No. PCT/IB2011/050091, filed Jan. 10, 2011, mailed Aug. 16, 2012, 14 pgs.
Dusemund; International Search Report and Written Opinion for serial No. PCT/IB2011/050091, filed Jan. 10, 2011, mailed Apr. 12, 2011, 3 pgs.

(56) References Cited

OTHER PUBLICATIONS

Huang et al.; "Optical coherence tomography", Science, vol. 254, No. 5035, S. 1178-1181 (1991).

Vakhtin et al.; "Common-path interferometer for frequency-domain optical coherence tomography"; Applied Optics, vol. 42, No. 34, S. 6953-6957 (2003).

Schonleber, Martin; Final Office Action for U.S. Appl. No. 13/667,809, filed Nov. 2, 2012, mailed Sep. 16, 2013, 9 pgs.

Schonleber, Martin; Issue Notification for U.S. Appl. No. 13/667,809, filed Nov. 2, 2012, mailed Feb. 25, 2015, 1 pg.

Schonleber, Martin; Non-Final Office Action for U.S. Appl. No. 13/667,809, filed Nov. 2, 2012, mailed Apr. 15, 2013; 12 pgs.

Schonleber, Martin; Non-Final Office Action for U.S. Appl. No. 13/667,809, filed Nov. 2, 2012, mailed Apr. 24, 2014; 8 pgs.

Schonleber, Martin; Notice of Allowance for U.S. Appl. No. 13/667,809, filed Nov. 2, 2012, mailed Dec. 4, 2014, 10 pgs.

Schonleber, Martin; U.S. Patent Application entitled: Material-Working Device with In-situ Measurement of the Working Distance, having U.S. Appl. No. 13/667,809, filed Nov. 2, 2012, 32 pgs.

Schonleber; International Preliminary Report on Patentability for serial No. PCT/IB2011/052048 filed May 10, 2011, mailed Nov. 22, 2012, 7 pgs.

Schonleber; International Search Report and Written Opinion for serial No. PCT/IB2011/052048 filed May 10, 2011, mailed Sep. 21, 2011, 2 pgs.

Michelt, Berthold; U.S. Patent Application entitled: Optical Measuring Device for Acquiring Differences in Distance and Optical Measuring Method, having U.S. Appl. No. 14/307,481, filed Jun. 17, 2014, 37 pgs.

Precitec Optronic Gmbh; International Search Report and Written Opinion for serial No. PCT/IB2014/062290, filed Jun. 17, 2014, mailed Sep. 22, 2014, 20 pgs.

Schonleber, Martin; International Search Report and Written Opinion for PCT/IB2013/060127, filed Nov. 14, 2013, mailed Mar. 21, 2014, 17 pgs.

Schonleber, Martin; U.S. Patent Application entitled: Optical Measuring Method and Measuring Device Having a Measuring Head for Capturing a Surface Topography by Calibrating the Orientation of the Measuring Head, having U.S. Appl. No. 14/713,150, filed May 15, 2015, 54 pgs.

Jakob, Dr. G., "Koaxiale Interferometrische Schichtdickenmessung", Optical Measuring, Sonderdruck aus Photonik Mar. 2000; 4 pgs.

Knuttel, Dr. Alexander; "Non-compact Roughness and 3D Topography Evaluation of grinded Wafers down to nm level", Dec. 1, 2010, 25 pgs.

German Examination Report for German Application No. DE102013010030.5, filed Jun. 17, 2013, mailed Feb. 28, 2014, 12 pgs.

Schonleber, Martin; Non-Final Office Action for U.S. Appl. No. 13/440,434, filed Apr. 5, 2012, mailed Jun. 25, 2015, 21 pgs.

Schonleber, Martin; Notice of Allowance for U.S. Appl. No. 13/440,434, filed Apr. 5, 2012, mailed Sep. 23, 2015, 11 pgs.

Michelt, Berthold; Applicant Interview Summary for U.S. Appl. No. 14/307,481, filed Jun. 17, 2014, mailed Nov. 20, 2015, 3 pgs.

Michelt, Berthold; Non-Final Office Action for U.S. Appl. No. 14/307,481, filed Jun. 17, 2014, mailed Aug. 26, 2015, 41 pgs.

German Examination Report for serial No. 102012111008.5, filed Nov. 15, 2012 , mailed Jun. 19, 2013, 17 pgs.

ISIS Sentronics Gmbh Data Sheet, "StraDex a3 sensor"; 3 pgs.

Malta, D. et al.; "Fabrication of TSV-Based Silicon Interposers", RTI International, 6 pgs.

Precitec Optronik Gmbh; French Preliminary Search Report and Written Opinion for serial No. FR1253225, mailed Nov. 13, 2013, 10 pgs.

Schonleber, Martin; Corrected Notice of Allowability for U.S. Appl. No. 13/440,434, filed Apr. 5, 2012, mailed Mar. 1, 2016, 6 pgs.

Schonleber, Martin; Issue Notification for U.S. Appl. No. 13/440,434, filed Apr. 5, 2012, mailed Mar. 9, 2016, 1 pg.

Schonleber, Martin; Notice of Allowance for U.S. Appl. No. 13/440,434, filed Apr. 5, 2012, mailed Jan. 13, 2016, 11 pgs.

Michelt, Berthold; Final Office Action for U.S. Appl. No. 14/307,481, filed Jun. 17, 2014, mailed Feb. 12, 2016, 24 pgs.

Michelt, Berthold; Notice of Allowance for U.S. Appl. No. 14/307,481, filed Jun. 17, 2014, mailed Jul. 25, 2016, 20 pgs.

Schonleber, Martin; Non-Final Office Action for U.S. Appl. No. 14/713,150, filed May 15, 2015, mailed Sep. 6, 2016; 50 pgs.

\* cited by examiner

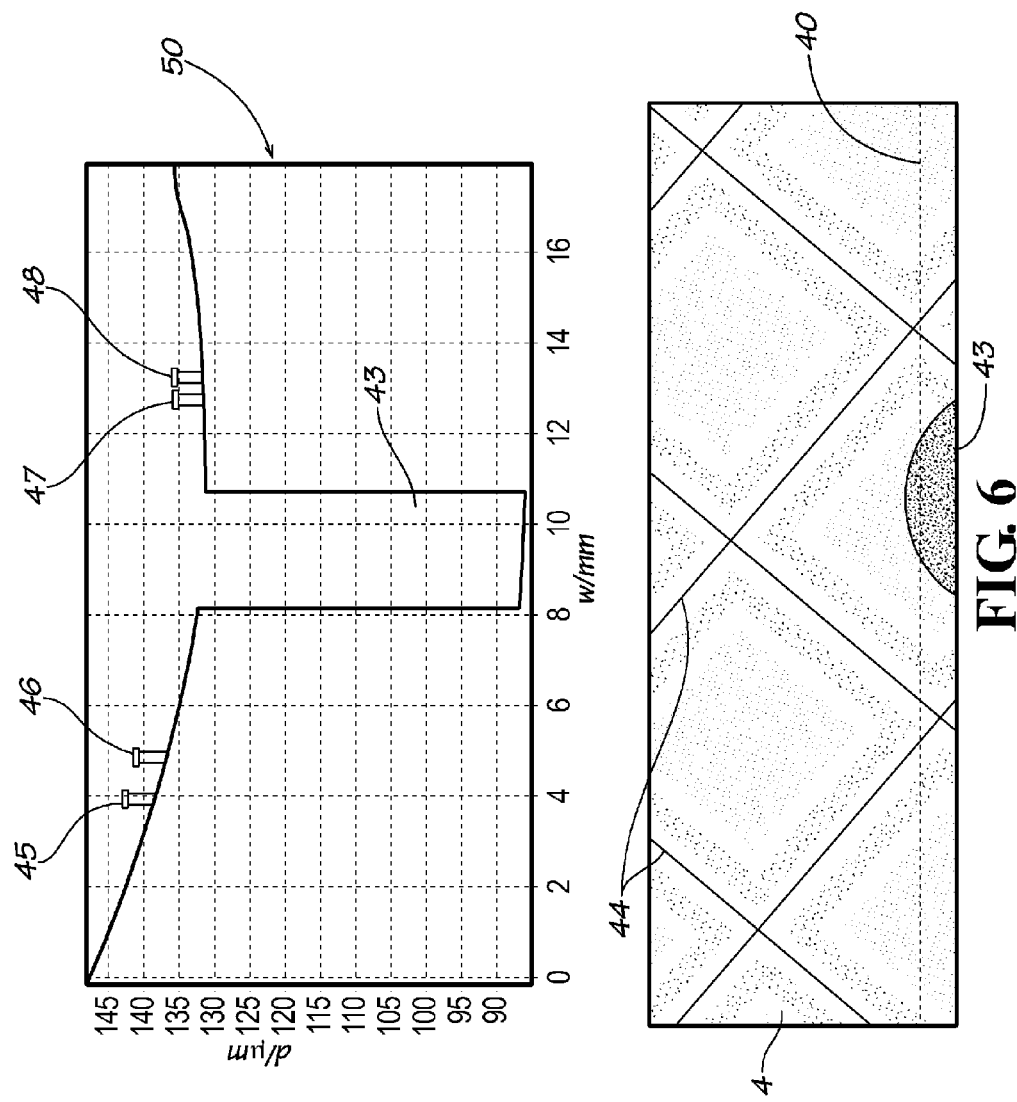

TEST DEVICE FOR TESTING A BONDING LAYER BETWEEN WAFER-SHAPED SAMPLES AND TEST PROCESS FOR TESTING THE BONDING LAYER

CROSS-REFERENCE TO RELATED APPLICATION

In accord with 35 U.S.C. §119, this application claims the benefit of Germany Patent Application serial number DE 10 2011 051146.6, filed Jun. 17, 2011, which is hereby incorporated herein by reference in its entirety.

FIELD

The invention relates to a test device for testing a bonding layer between wafer-shaped samples and a test process for testing the bonding layer.

BACKGROUND

Applications for bonding layers of wafer-shaped samples are known from the article entitled "Adhesive Wafer Bonding" by F. Niklaus, G. Stemme, J.-Q. Lu and R. J. Gutmann published in the Journal of Applied Physics, Applied Physics Reviews—Focused Review, Vol. 99, No. 1, pp. 031101.1 to 031101.28, 2006. The bonding layers used are usually polymer adhesive layers that are applied to one or both of the wafer-shaped samples to be bonded. Once the surfaces of the samples covered with the polymer adhesive have been bonded, pressure or force is applied to the wafer-shaped samples. A temperature treatment is also typically used to reinforce the bonding process.

The bonding and production of a bonding layer between wafer-shaped samples is thus a relatively simple, robust and inexpensive process, wherein the bond strength and the formation of cavities on the surfaces to be bonded can be influenced by the type of polymer adhesive used. The quality of the bonding layer is determined by the degree of polymerisation of the polymer adhesive, the wafer-shaped sample material, the size of foreign particles on the wafer surface and the wafer topography, the polymer thickness, the polymer viscosity during production of the bonding layer and the bond pressure applied to the two wafer-shaped samples. While foreign particles in the bonding layer can be tolerated as long as they remain smaller than the thickness of the bonding layer, cavities and adhesive interruptions within the bonding layer cannot be tolerated and can lead to rejection.

In some applications in semiconductor technology, for example, silicon wafers with a thickness of the order of a few tens of µm (micrometers) and diameters of over 10 inches or 250 mm are produced and processed. Such silicon wafers behave like an aluminium foil, for example, and cannot be handled or processed using standard tools. Such wafer-shaped samples warp in such a manner that they cannot even be transported or stored in a wafer cassette. For this reason thin wafer-shaped samples of this type are processed using the bonding layer on a carrier wafer, a thin functional wafer thus being held and stabilised by a stable carrier waver using the bonding layer.

In manufacturing thin wafers of this type as functional wafers it has proved useful to grind the functional wafer down to a thickness of a few tens of µm as indicated above. Once the functional wafer with its finished functional face is bonded onto the carrier wafer, a composite comprising a bonding layer and wafers is held together during grinding by means of the bonding layer. During grinding in particular bonding layer regions with reduced adhesive layer thickness or with interruptions or air bubbles in the adhesive layer are extremely critical since it is here that mechanical stresses capable of destroying the functional wafer can occur. For this reason it is advantageous to examine the entire surface of the adhesive layer for cavities and defects to an accuracy of less than one millimeter prior to grinding.

To this end wafer-shaped samples with the aforementioned diameter of, for example, more than 10 inches can be point scanned with a spiral motion. At a rate of 4 kHz and a step width of 1 mm with a diameter of 300 mm this requires a test time of approximately 70 seconds. The measurement is preferably made through the carrier wafer because the bonding layer cannot be measured reliably through the functional wafer using an optical method due to unevennesses in the structure, due to the inhomogeneity of light absorption caused by doping substances and due to metallised layers on the functional wafer used as the wafer-shaped sample.

A measuring head configured for an OCT (Optical Coherence Tomography) process, in particular for an FD-OCT (Frequency or Fourier Domain Optical Coherence Tomography) process, is known from publication WO 2006/028926 A1.

A measuring head for the OCT process with a reference arm or a reference plane is able to record the absolute distances between a reference face and any surface on a measurement object as well as measuring the layer thickness. A rotating disc positioned in the reference arm such that it is able to rotate has proved useful for this purpose because with this partially coated disc it is possible to achieve phase shift. However, this disc provides no support for the attribution and classification of measured layer thickness peaks and distance peaks which cannot be clearly classified as layer thickness measurements or distance measurements without prior knowledge of the layer structure of a measurement object.

SUMMARY

The object of the invention is therefore to enable the defects occurring in a bonding layer to be classified quickly and accurately using the OCT process and to create a test device suitable for this process.

The object is achieved by means of the subject matter of the independent claims. Advantageous developments of the invention are detailed in the dependent claims.

The invention provides a test device for testing a bonding layer between wafer-shaped samples and a test process for testing the bonding layer. The test device comprises a measuring head configured for an OCT process that directs an optical measuring beam at a composite comprising at least two wafer-shaped samples with a bonding layer positioned between them. An optical beam splitter plane is configured to divert an optical reference beam as a reference arm for distance measurements. An evaluation unit is configured to evaluate layer thickness measurements without a reference arm and distance measurements with a reference arm. An optical switch device is configured to connect and disconnect the reference arm.

A device of this type has the advantage that it enables layer thickness profiles and distance profiles to be measured in quick succession. Furthermore, it makes it possible to carry out a profile scan that alternately records layer thickness and distance at the same scan positions. Thus it is possible using this device both to obtain accurate prior knowledge of the layer structure of a bonding layer between wafer-shaped samples and to classify a measurement peak clearly either as a layer thickness peak of a layer thickness measurement or a distance peak of a distance measurement.

The device is advantageously able to mask out the reference arm required for OCT process distance measurements when layer thicknesses are to be recorded and to connect it again when a distance measurement is to be made. Moreover, with the test device it should be possible to avoid the astigmatism and coma effects which can occur in a converging measuring beam, generally at a beam splitter plate, and to divert an astigmatism- and coma effect-free reference arm from the measuring beam for the distance measurement.

In one embodiment of the invention a beam splitter cube able to overcome the optical disadvantages set out above is therefore preferably provided as the beam splitter in the measuring beam rather than a beam splitter plate. It is also possible to create a fibre-optic test device in which these disadvantageous effects of a plate-shaped optical beam splitter are overcome by the use of a fibre-optic circulator. Light for the measuring head and for the reference arm can be decoupled simultaneously from this type of fibre-optic circulator which receives light from a light source. The measuring head, the reference arm and the light source are thus connected to the circulator.

Furthermore, a fibre-optic test device has the advantage that the measuring head can be positioned at a distance from an evaluation unit comprising light source, interferometer, reference arm and optical switch device for the reference arm and thus at a distance from the actual test object.

A further embodiment of the invention provides for the use of an optical deflector configured to deflect the reference arm from the beam splitter plane as an optical switch device. In this process it is advantageous for the deflector not to be aligned orthogonally in relation to the reference beam, but for its surface normal to be angled such that any reflections on a surface of the deflector cannot be coupled into the measuring beam itself but are deflected into an uncritical region of the test device.

In a further embodiment of the invention a bistable electrical switch configured to push a diaphragm into and out of the reference beam or to open and close an iris diaphragm can be provided as the optical switch device. Here, too, however the surface normals of the diaphragms are positioned such that they do not send any components of the reference beam back to the beam splitter. Such diaphragms have the advantage compared to optical deflectors that they do not exert any pivoting or pushing movement and thus allow shorter scanning times.

A further embodiment can have an optical liquid crystal block as an optical switch device. Liquid crystals allow the reference arm to be optically disconnected almost inertia-free by applying a low electrical voltage to a liquid crystal structure such that the face of the crystal structure prevents the reference beam from passing through two coordinated polarisation filters by rotating a polarisation plane between the polarisation filters.

In this embodiment the test device also comprises a switch module with a measuring head and an optical switch device. A module of this type has the advantage of compact structure and the whole test device can thus be positioned in a single housing above a test object.

Moreover, a test device can also have a modified Michelson interferometer with a reference arm which can be masked out by the optical switch device and with a free optical arm for monitoring the test object which can have a camera or an eyepiece. A modified Michelson interferometer to which an OCT process evaluation unit is connected can be produced relatively inexpensively and be used close to the test object.

In contrast, fibre-optic test devices can be configured such that they have a fibre-optic reference arm and an evaluation unit at a distance from the test object. To this end a semi-transparent mirroring layer is positioned at the output from the measuring head at the transition to a fibre-optic optical waveguide such that a part of the light beam coupled into the measuring head is coupled back to the evaluation unit and into a device with fibre-optic reference arms via a fibre-optic cable and a circulator.

The fibre-optic reference arms preferably have Faraday mirrors at their ends as fibre-optic reflectors. Furthermore, it is possible to provide a plurality of fibre-optic reference arms with different optical lengths pre-programmed for different distance measurements in the region of the evaluation unit positioned a distance from the test object. Thus it is possible to couple different fibre-optic reference arms to the measuring head via the aforementioned fibre-optic circulators.

It is also possible to provide a fibre-optic reference arm without final mirroring of the optical fibres such that it acts as a blocked reference arm since no reflected wave for interference is able to form in it. Positioned upstream of these various fibre-optic reference arms is a fibre switch pre-programmed to switch between the different reference arms and thus between a blocked reference arm and reference arms with different optical lengths.

Moreover, it is also possible to provide a fibre coupler that both couples a fixed reference arm to the circulator and is able to couple the fibre switch to the circulator. By means of the reflecting fibre end at the measuring head, sub-waves reflected at the fibre-optic reflectors on the reference arms are thus superimposed on the optical measurement lengths of the measuring head measuring beam by reflection. Finally, the resulting reference images are evaluated by a spectrometer connected to the circulator.

A test process for testing a bonding layer between wafer-shaped samples using one of the embodiments of the aforementioned test device has the following steps. Firstly, an areal layer thickness image of the bonding layer is created using the OCT process. A layer thickness image of this type allows the initial identification of defect regions which can subsequently be examined more closely by positioning a measuring head on one of the identified defect regions in the bonding layer by narrowing a depth measurement range to a few interference maxima.

As it is awkward to measure thin layers with a sensor with a large measuring range, this measuring range of a few interference maxima which, though narrowed, remains sufficiently large is advantageously used in the measuring process, firstly due to the lack of sensitivity of a large measuring range and secondly because it is impossible to evaluate a layer thickness below 2 interference maxima. In so doing, however, layer thickness measurement peaks and distance measurement peaks of the intensity of an intensity image generated by an interferometer are compressed into a narrow range, thereby making classification of the intensity measurement peaks as layer thickness measurement peaks or layer thickness peaks and distance measurement peaks or distance peaks more difficult.

In this embodiment of the process, therefore, a layer thickness profile is first measured along a measuring track in the defect region with the test device reference arm disconnected; then a distance measurement profile is measured on the same measuring track with the test device reference arm reconnected. This is followed by a profile scan during which layer thickness measurements with disconnected reference arm and distance measurements with connected reference arm are performed alternately at identical scan positions on the measuring track.

The evaluation unit then compares the profile scan with the layer thickness profile and the distance profile to classify the measured peak values as either thickness measurement values or distance measurement values. This process advantageously obtains exact prior knowledge of the layer structure before determining the position of the virtual reference plane so that the peaks identified can be correctly attributed. It also ensures that the expected ranges do not overlap.

Using this process it is possible to create in an advantageous manner a measurement graph for evaluating the classification of measurement values with regard to a defect region in a bonding layer between wafer-shaped samples. Finally, using the classified layer thickness and distance measurements in the defect region it is possible to classify a defect as a tolerable foreign particle in the bonding layer or a non-tolerable cavity in the bonding layer. If the evaluation reveals a cavity in the bonding layer, such a composite comprising a bonding layer and wafer-shaped samples cannot be subject to a grinding process. In fact, the bonding layer will have to be remade free of cavities.

Moreover, the process also has the advantage of identifying warped areas in a surface of the composite comprising two samples with a bonding layer positioned between by calculating distance values between the measuring head and the surface of the composite with the test device reference arm connected without the need for an additional step in the process since the warped area is identified automatically by the distance profile measurement already carried out.

The test device has a measuring head for a FD-OCT process that directs an optical measuring beam at a composite consisting of at least two wafer-shaped samples with a bonding layer positioned between them. An optical beam splitter plane is configured to divert an optical reference beam as a reference arm for distance measurements.

DESCRIPTION OF THE FIGURES

The invention is now explained in greater detail with reference to the attached figures.

FIG. 6 is a schematic representation of a test result for a bonding layer in the region of a defect in the bonding layer.

DETAILED DESCRIPTION

Figure 1:
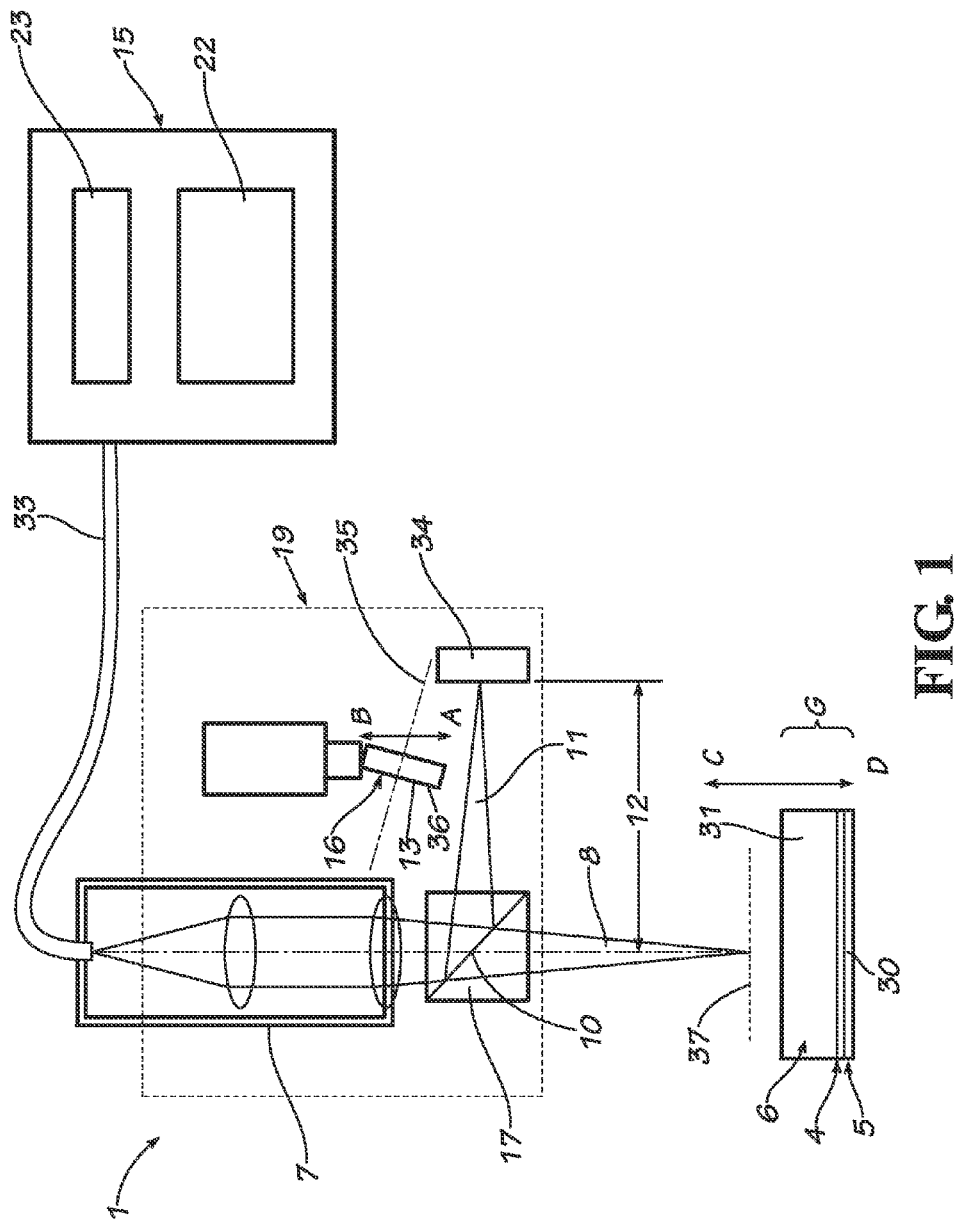
FIG. 1 is a schematic drawing of a test device as disclosed in a first embodiment of the invention.

FIG. 1 shows a schematic drawing of a test device 1 as disclosed in a first embodiment of the invention. The test device 1 has a measuring head 7 which directs an optical measuring beam 8 at a composite 9, the measuring beam 8 recording the quality of a bonding layer 4 between two wafer-shaped samples 5 and 6 with regard to defects.

To this end an optical reference beam 11 is decoupled from the measuring beam 8 using a beam splitter cube 17 that generates a reference image in the beam splitter plane 10 which can be evaluated via the fibre connection 33 between the measuring head 7 and an evaluation unit 15, the evaluation unit 15 having a spectrometer 22 that records the interference image and the spectral interference pattern with regard to both intensity peaks of a layer thickness measurement and intensity peaks of a distance measurement.

In this process the intensity peaks of the layer thicknesses are generated solely by the interference of the two boundary faces that are formed at the transitions of the bonding layer to the wafer-shaped samples. The intensity peaks of the distance measurement are formed by interferences in the beam splitter plane 10 between the measuring beam 8 and the reference beam 11, the reference beam 11 being projected from a reflector 34 at the end of a reflector arm 12 onto the beam splitter plane 10. Allocation or classification of the intensity peaks from the layer thickness measurement and the distance measurement recorded by the interferometer 22 is difficult and, in the case of the tightly packed intensity maxima which occur in the examination of defects in bonding layers 4, inconclusive.

In order to improve classification/attribution in a reproducible manner, in addition to the measuring head 7 and the beam splitter cube 17 for the reference arm 12 the test device 1 also has in a switch module 19 an optical switch device 16 which pushes an optical deflector 13 into the reference arm 12 in the direction of arrow A and out of it in the direction of arrow B. Thus in position A intensity peaks can be attributed to the layer thickness measurement and in position B intensity peaks can be attributed to the superimposition of the layer thickness measurement and the distance measurement.

By means of an appropriate comparison using the evaluation unit 15 of measurements with an interrupted reference beam 11 and measurements with a non-interrupted reference beam 11, it is then possible to make a clear distinction between layer thickness peak values of the reflected intensity image and intensity peaks of the distance measurement.

To avoid reflections from the surface of the optical deflector 13 hitting the optical beam splitter plane 10 and thus distorting the measurement result as the optical deflector 13 is moved into the reference arm 12, the surface normal 35 to the surface 36 of the optical deflector 13 is angled such that reflections on the surface 36 of the optical deflector 13 are directed at a non-critical region inside the switch module 19 and do not affect the optical beam splitter plane 10 of the beam splitter cube 17 when being moved into the reference arm 12 or into the position of the reference arm 12. The optical switch device 16 is thus different from the rotating disk with fibre pusher known from the aforementioned WO 2006/028926 A1 which is positioned in the reference arm.

As shown in FIG. 1, the composite comprising one bonding layer 4 between two wafer-shaped samples 5 and 6 is still positioned outside the measuring plane 37 and can be pushed mechanically into the measuring plane 37 in the direction of arrow C by a corresponding measuring table with the composite 9 comprising a functional wafer 30 and a carrier wafer 31 between which is positioned the adhesive layer to be examined. The measuring beam 8 is able to register the bonding layer 4 through the carrier wafer 31. This arrangement of wafer-shaped sample and bonding layer 4 is selected because a functional wafer 30 may have optically effective layers such as metallised layers or highly doped zones which could lead to misinterpretations in respect of the quality of the bonding layer 4. By contrast, the carrier wafer can be selected such that for example it is evenly transparent like a silicon wafer for an infrared light source so that defects in the bonding layer 4 can be recorded using this test device as shown schematically in FIG. 1. After the measurement the composite 9 consisting of the bonding layer 4 and wafer-shaped samples 5 and 6 can be removed from the measuring plane 37 in the direction of arrow D or, if the bonding layer 4 is free of cavities, the functional wafer can be ground.

In addition, the light from a broadband light source 23 is sent from the evaluation unit 15 to the measuring head 7 via the fibre connector 33. Furthermore, in this embodiment of the test device 1 a beam splitter cube 17 rather than a semi-transparent beam splitter plate was used in the beam splitter plane 10 to avoid the astigmatism and coma effects which occur in a converging measuring beam when using a semi-transparent plate.

Figure 2:
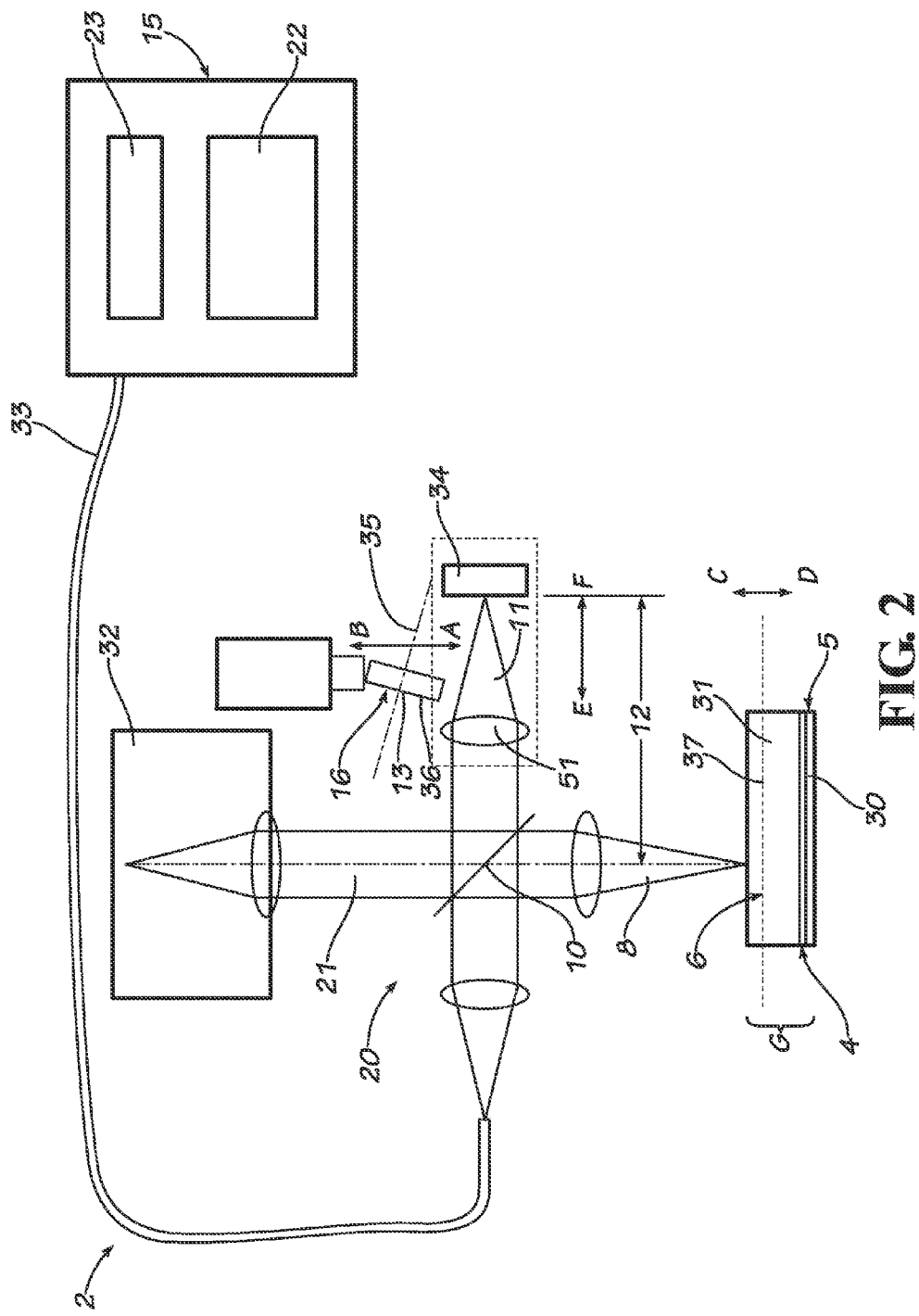
FIG. 2 is a schematic drawing of a test device as disclosed in a second embodiment of the invention.

FIG. 2 shows a schematic drawing of a test device 2 as disclosed in a second embodiment of the invention. Components with functions identical to those in FIG. 1 are given the same reference numerals and are not discussed in further detail.

In this embodiment a light source is sent to a Michelson interferometer 20 via a fibre connector 33. The Michelson interferometer 20 differs from the first embodiment disclosed in FIG. 1 in that the beam splitter plane 10 is positioned in a collimator region such that a semi-transparent mirror or semi-transparent mirror plate can be used as an optical beam splitter as astigmatism and coma effects are negligible in a collimator region with a parallel beam.

Furthermore, the Michelson interferometer 20 also differs from the embodiment disclosed in FIG. 1 in that the reflector 34 can be pushed in the direction of the arrows E and F, thereby making it possible to lengthen and shorten the reference arm 12 and thus over a limited area to shift the measuring plane 37 in the measurement object consisting of a composite 9 comprising a bonding layer 4 between wafer-shaped samples 5 and 6 in the direction of the arrows C and D without increasing the height of the sample holder table.

In a further version both the reflector 34 and a focussing lens 51 placed in front of it can be pushed in the direction of the arrows E and F. This helps to avoid losses due to defocusing.

For this test device the Michelson interferometer 20 also has the optical switch device 16 with optical deflector 13 already shown in FIG. 1. To avoid reflections of the optical deflectors 13 which would distort the measurement results, the surface 36 is not aligned orthogonally in relation to the reference beam 11. Instead of an optical deflector 13 it is possible to use other means to disconnect the reference arms 12 such as, for example, a liquid crystal panel able to interrupt or reconnect the optical path of the reference arm using a low switching voltage. It is also possible to use shutters such as iris diaphragms since for the devices shown in FIGS. 1 and 2 it is important to ensure that the surface normal 35 of the diaphragms is aligned at an angle to the orthogonal of the reference beam to avoid distortions of the measurement result due to reflections on the closed diaphragms.

As the Michelson interferometer 20 has a free optical arm 21 as shown in FIG. 2, additional optical means can be sent to the beam splitter plane 10 via this free optical arm 21 such as, for example, means for coupling in a pilot laser spot which is helpful in case of infrared measuring light, or means for coupling in a measuring light via an external light source which can be used to couple in a second layer thickness sensor for example with a different spectral and measurement range or with other spot positions. Finally, it is also possible to connect a camera 32 or eyepiece or object lights to the free optional arm of the Michelson interferometer 20 for observing the object.

Figure 3:
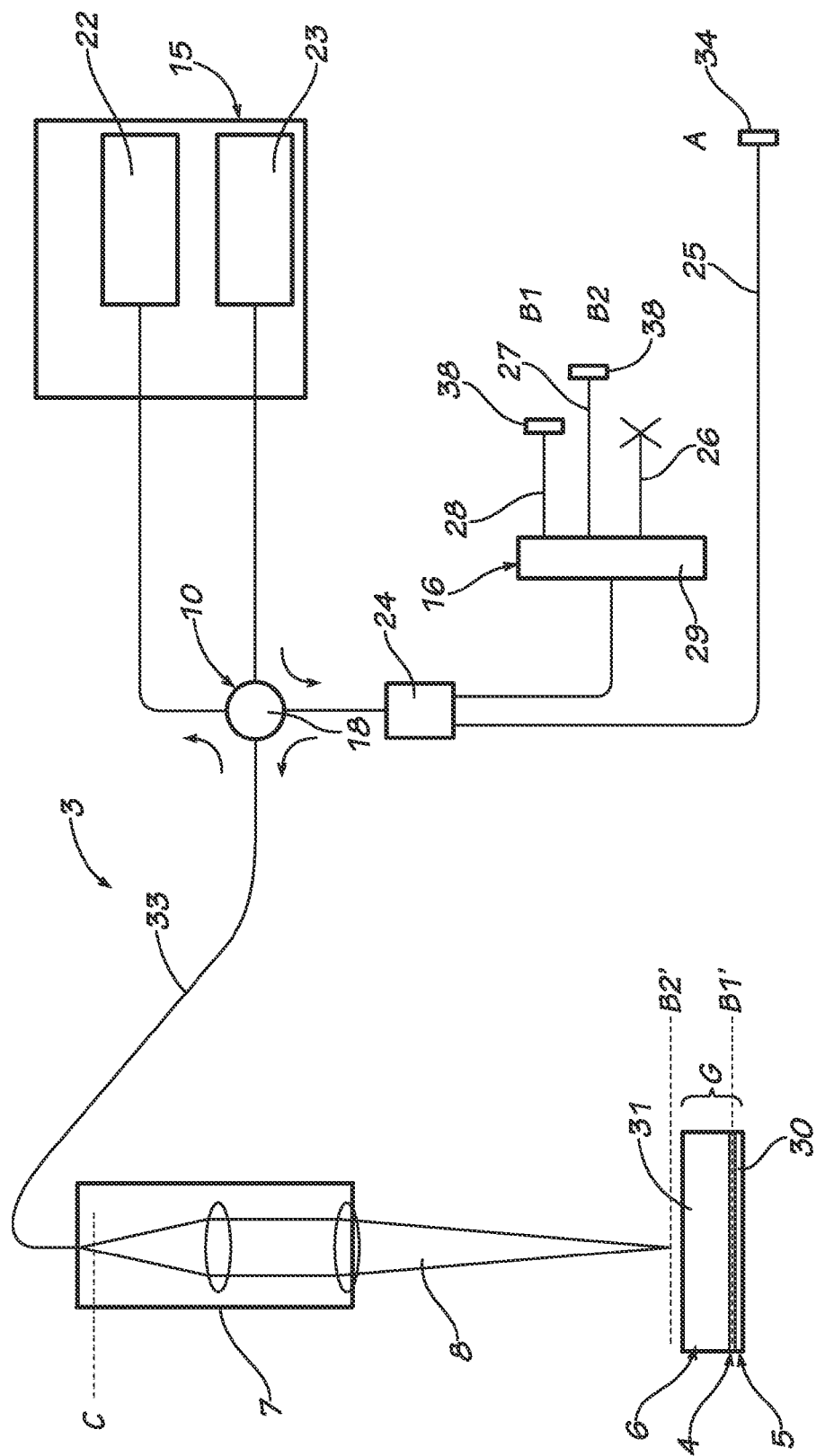
FIG. 3 is a schematic drawing of a test device as disclosed in a third embodiment of the invention.

FIG. 3 shows a schematic drawing of a test device 3 as disclosed in a third embodiment of the invention. This test device is a fibre-optic test device and has a semi-transparent reflector at the measuring light input C of the measuring head 7 at the transition to the fibre-optic connector 33. This makes it possible to provide beam splitting, to fit or provide a reference arm and to switch or interrupt the reference arm at a distance from the measuring head 7. The structure of the measuring head 7 is thus simpler than those in the embodiments shown in FIGS. 1 and 2.

A fibre-optic circulator 18 is then used instead of a beam splitter plane 10, the fibre-optic circulator connecting both the light source 23 of the evaluation unit 15 and the interferometer 22 to the measuring head 7 and a fibre coupler 24. The fibre coupler 24 is connected to a fibre switch 29 as the optical switch device 16 and can also be coupled to a reflector mirror 34 of a fibre-optic reference arm 25. The fibre switch 29 makes it possible to connect fibre-optic reference arms with different optical path lengths such that a reference arm of this type with a Faraday reflector 38 at end B1 is able to form interferences with a virtual plane B1' lying in the plane of the bonding layer 4 of the composite 9.

A reference signal can be sent from the Faraday reflector 38 at the end of B1 via the fibre switch 29, the fibre coupler 24 and the circulator 18 to the interferometer 22 in the evaluation unit 15. Furthermore, the fibre switch 29 makes it possible to switch from a reference arm 28 to B1 or from a reference arm 27 to B2 or to a blocked reference arm 26. In practical terms the blocked reference arm assumes the function of the optical deflector 13 in the embodiments disclosed in FIGS. 1 and 2. To this end the optical fibre is introduced into a black reflection-free light absorber. The advantage of this fibre-optic test device is a relatively small measuring head 7 which is able to examine bonding layer quality on site without the need for vibration-sensitive beam splitters or other additional elements such as the optical deflector at the place of measurement.

Figure 4:
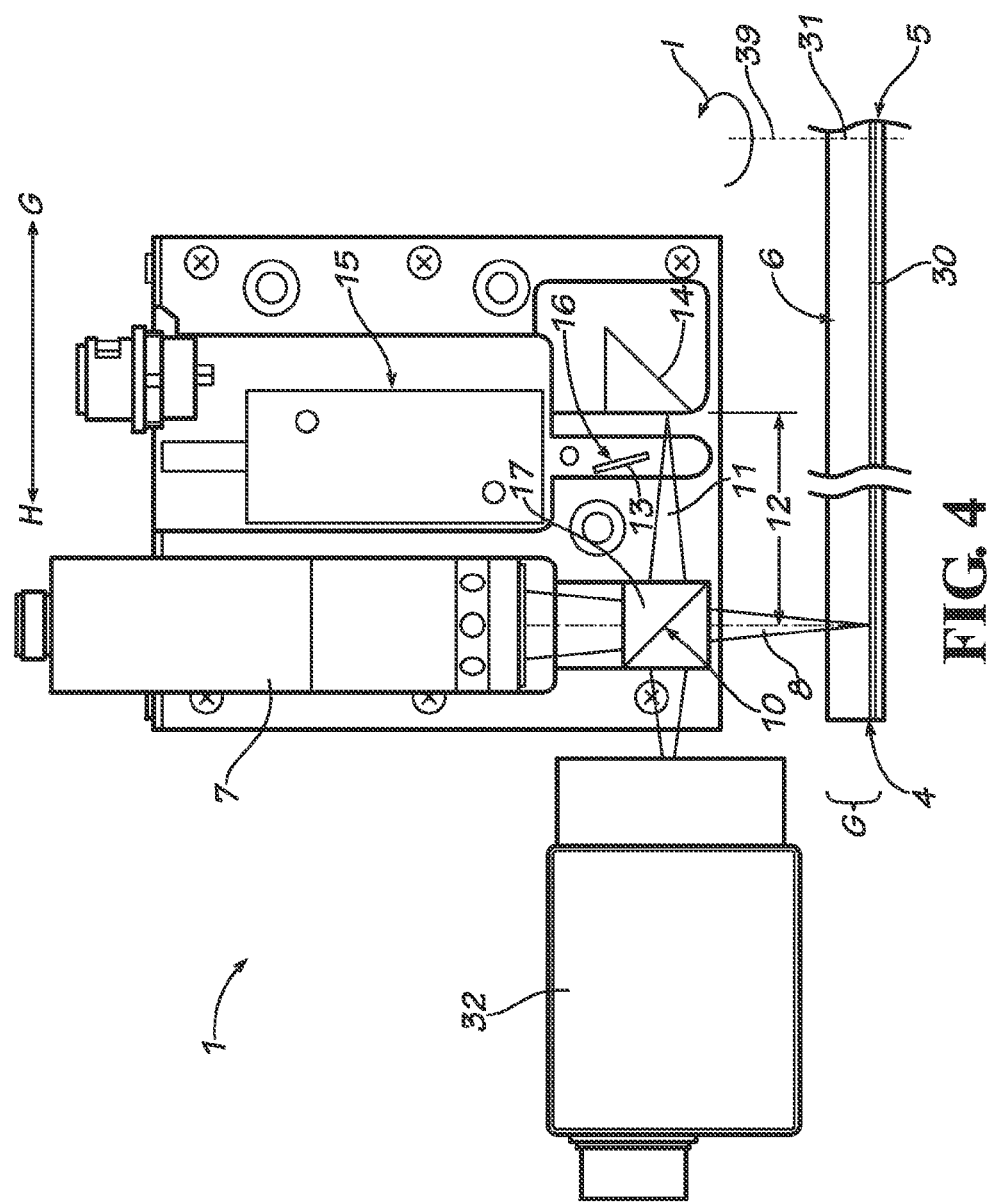
FIG. 4 is a schematic representation of a structure of a test device as disclosed in FIG. 1.

FIG. 4 shows a schematic drawing of a structure of a test device 1 as disclosed in FIG. 1. In contrast to the on-site fibre-optic test device, this structure comprises not only the measuring head 7, but also the optical switch device 16, the beam splitter cube 17 and the reference arm 12 with a reference mirror 14 and thus has a relatively compact structure. Optionally, it can also be supplemented by a flange-mounted camera 32 to display the quality of the bonding layer 4 between a carrier wafer 31 and a functional wafer 30.

A composite of this type comprising a functional wafer 30 and a carrier wafer 31 may, for example, have a diameter of 300 mm, the disc-shaped composite 9 rotating about an axis 39 in the direction of arrow I on a turntable, while the measuring device 1 is moved either towards the axis 39 in the direction of arrow G or away from the axis 39 in the direction of arrow H such that the disc-shaped composite 9 is scanned in a spiral pattern.

At a scanning frequency of 4 kHz and a scanning distance of one millimeter both circumferentially and radially in relation to the disc-shaped composite 9, it is possible to examine a bonding layer 4 for defects within a period of approx. 70 seconds. If the scanning distance is reduced to 0.25 mm, a total scanning time of approx. 20 minutes is required to quality control a disc-shaped composite 9 with a diameter of 300 mm. It therefore appears sensible to start by carrying out a layer thickness measurement of the entire disc to locate defects and then to examine these defects more closely using the possibility of connecting and disconnecting a reference arm 12 as shown in FIGS. 1 to 4 in order to establish whether they are simply tolerable foreign particles included in the bonding layer without damaging the composite or cavities which should be avoided if the functional wafer is to be ground.

Figure 5:
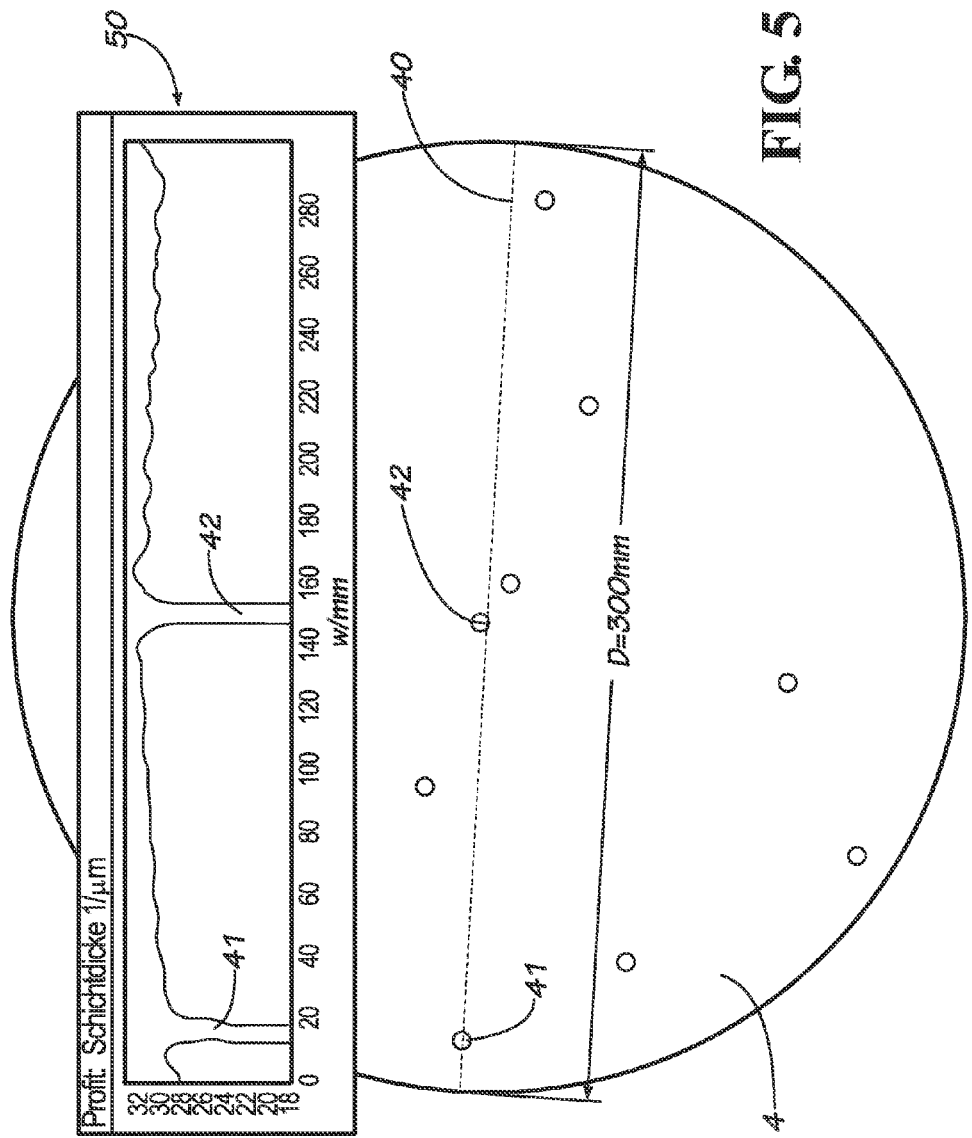
FIG. 5 is a schematic representation of a test result for a bonding layer between two wafers.

FIGS. 5 and 6 show results of large-surface, spiral layer thickness scans and of detailed measurements taken along a measurement track to characterise and classify defects.

FIG. 5 shows a schematic representation of a test result for a bonding layer 4 between two wafers with clearly recognisable defects after a layer thickness measurement carried out in a spiral on a wafer with a diameter D=300 mm. The initial layer thickness measurement indicates several defects including, for example, defect 41 and defect 42, which require further investigation. This is done using the test devices discussed above which by virtue of a measurement track 40 make it possible to classify exactly whether the intensity maxima of the OCT process recorded by the spectrometer represent scanning peaks or layer thickness measurement peaks; the layer thickness can thus be clearly distinguished from the distance and layer thickness diagram shown in FIG. 5 can be printed out. In addition, the measurement position w in millimeters is indicated on the x-axis while the layer thickness d in micrometers is indicated on the y-axis. This diagram shows that the two defects 41 and 42 are caused by cavities in the bonding layer since the layer thickness d in the defect areas 41 and 42 falls from the average layer thickness of approx. 30 µm to below 20 µm.

In order to reduce the measurement times, the measurement track 40 can be shortened considerably as shown in FIG. 6. Here too the layer thickness of a relatively thick bonding layer with an average thickness d of d>130 µm along a width w of approx. 17 mm is examined and a defect 43 is sectioned in order to establish whether it is a tolerable foreign particle defect or a cavity. As shown in the evaluation diagram 50, defect 43 is caused by a cavity in the bonding layer 4. In addition, regular quadratic tracks 44 can be seen on the bonding layer 4. These form the mesa structures 45, 46, 47 and 48 of the bonding layer. The mesa structures 45, 46, 47 and 48 of the bonding layer show that the quadratic tracks 44 reflect prepared singulation lines in the functional wafer which are cut approx. 5 µm deep into the functional wafer.

That which is claimed is:

1. A test process for testing a bonding layer, the test process comprising:
creating a flat layer thickness image of the bonding layer with a test device through an OCT process, the test device comprising:
a layer thickness measuring head configured for the OCT process, the measuring head directing an optical measuring beam at a composite comprising at least two wafer-shaped samples with the bonding layer positioned between them,
an optical beam splitter plane configured to divert an optical reference beam from the optical measuring beam as a reference arm for distance measurements, and
an evaluation unit configured to evaluate layer thickness measurements without the reference arm and distance measurements with the reference arm;
setting the measuring head to an identified defect area of the bonding layer by narrowing a depth measurement range to less than 10 interference maxima;
optically disconnecting the reference arm via an optical switch device;
measuring a layer thickness profile along a measurement track in the defect area of the bonding layer;
optically connecting the reference arm via the optical switch device;
measuring a distance profile on the measurement track in the defect area of the bonding layer;
taking a profile scan of the bonding layer with alternating layer thickness measurements and distance measurements at a scan position on the measurement track, wherein the layer thickness measurements are measured with the reference arm optically disconnected and the distance measurements are measured with the reference arm optically connected;
comparing the profile scan with the layer thickness profile and the distance profile in order to classify a measured value as a thickness measurement value or a distance measurement value.

2. The process of claim 1, further comprising:
evaluating the classification of the measured value in relation to the defect area on the bonding layer; and
producing a measurement graph.

3. The process of claim 1, further comprising classifying the measured value of the defect area as a foreign particle in the bonding layer or a cavity in the bonding layer.

4. The process of claim 1, further comprising identifying warped sections on a surface of the composite by optically connecting the reference arm of the test device and calculating a distance value between the measuring head and the surface of the composite.

* * * * *